(12) United States Patent
Tsalach-Weiss et al.

(10) Patent No.: US 11,986,187 B2
(45) Date of Patent: May 21, 2024

(54) CIRCULAR STAPLING DEVICE WITH INTEGRATED VISUALIZATION DEVICE

(71) Applicant: Covidien LP, Mansfield, MA (US)

(72) Inventors: Adi Tsalach-Weiss, New Haven, CT (US); Drew R. Seils, Guilford, CT (US); Steven H. Joyce, Durham, CT (US); David Scampoli, South Glastonbury, CT (US); Stephen R. Paul, East Hartford, CT (US); Kelly A. Azeredo, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 22 days.

(21) Appl. No.: 17/568,061

(22) Filed: Jan. 4, 2022

(65) Prior Publication Data
US 2022/0240939 A1 Aug. 4, 2022

Related U.S. Application Data

(60) Provisional application No. 63/143,405, filed on Jan. 29, 2021.

(51) Int. Cl.
*A61B 17/115* (2006.01)
*A61B 1/00* (2006.01)
*A61B 1/313* (2006.01)
*A61B 17/00* (2006.01)

(52) U.S. Cl.
CPC ...... *A61B 17/1155* (2013.01); *A61B 1/00121* (2013.01); *A61B 1/3132* (2013.01); *A61B 2017/00057* (2013.01)

(58) Field of Classification Search
CPC ............. A61B 1/00121; A61B 1/3132; A61B 2017/00057; A61B 17/1155
See application file for complete search history.

(56) References Cited

U.S. PATENT DOCUMENTS

| | | |
|---|---|---|
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

International Search Report dated May 16, 2022, issued in corresponding international application No. PCT/US2022/012846, 4 pages.

*Primary Examiner* — Aaron B Fairchild
(74) *Attorney, Agent, or Firm* — Carter, DeLuca & Farrell LLP

(57) ABSTRACT

A surgical stapling device includes a visualization device that extends through a body of the stapling device to facilitate visualization of tissue that surrounds an end effector of the stapling device. An anvil assembly of the surgical stapling device is adapted to facilitate passage of the visualization device through the anvil assembly.

18 Claims, 10 Drawing Sheets

(56) References Cited

U.S. PATENT DOCUMENTS

| | | | |
|---|---|---|---|
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A * | 6/1988 | Green | A61B 17/115 606/220 |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,144 A | 11/1995 | Guy et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | |
|---|---|---|
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |

(56) References Cited

U.S. PATENT DOCUMENTS

| | | |
|---|---|---|
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2004/0195289 A1* | 10/2004 | Aranyi ............... A61B 17/115 |
| | | 227/19 |
| 2005/0023325 A1* | 2/2005 | Gresham ............ A61B 17/115 |
| | | 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0108393 A1* | 5/2006 | Heinrich .......... A61B 17/00491 |
| | | 227/179.1 |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |

(56) References Cited

U.S. PATENT DOCUMENTS

| | | |
|---|---|---|
| 2015/0173763 A1 | 6/2015 | Liu |
| 2015/0209045 A1 | 7/2015 | Hodgkinson et al. |
| 2017/0128068 A1 | 5/2017 | Zhang et al. |

FOREIGN PATENT DOCUMENTS

| | | |
|---|---|---|
| CN | 203379175 U | 1/2014 |
| CN | 104039244 A | 9/2014 |
| CN | 104042288 A | 9/2014 |
| CN | 104367360 A | 2/2015 |
| CN | 209252996 U | 8/2019 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2019130087 A1 | 7/2019 |

\* cited by examiner

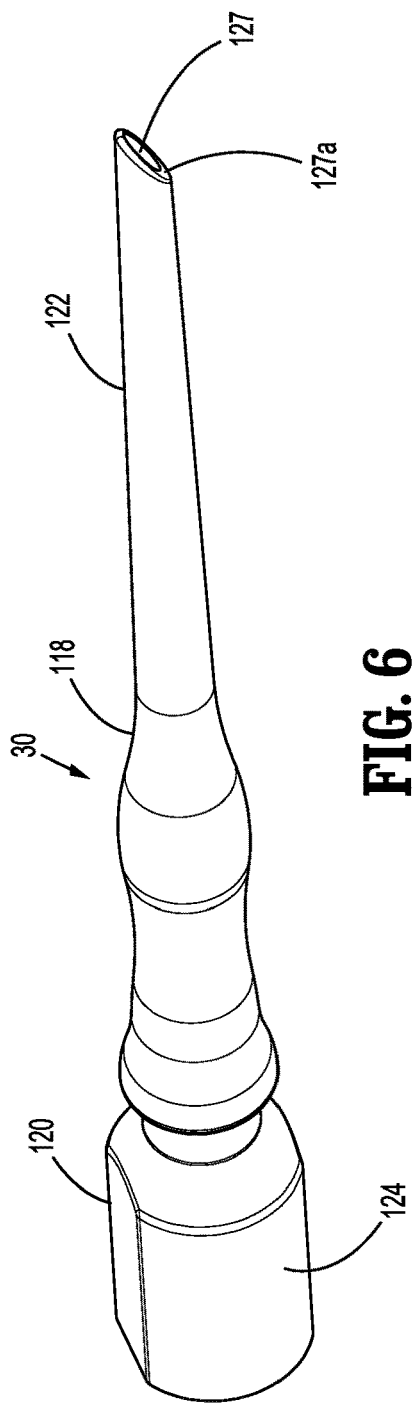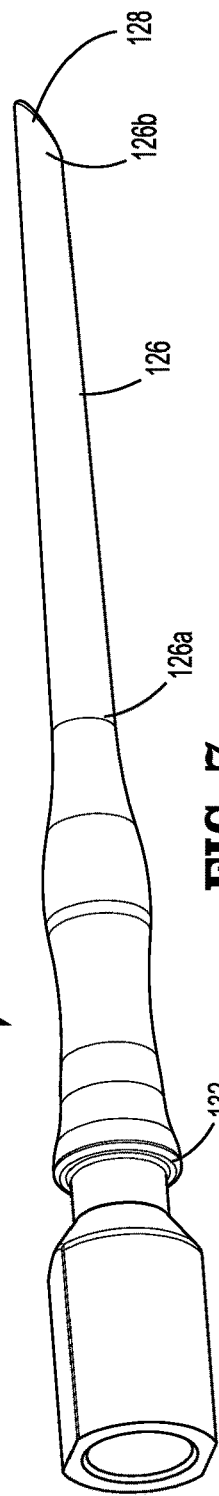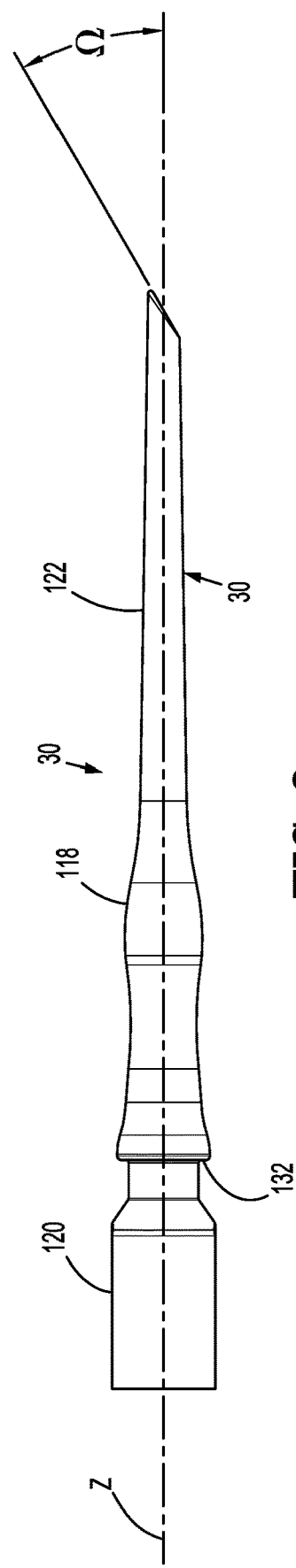

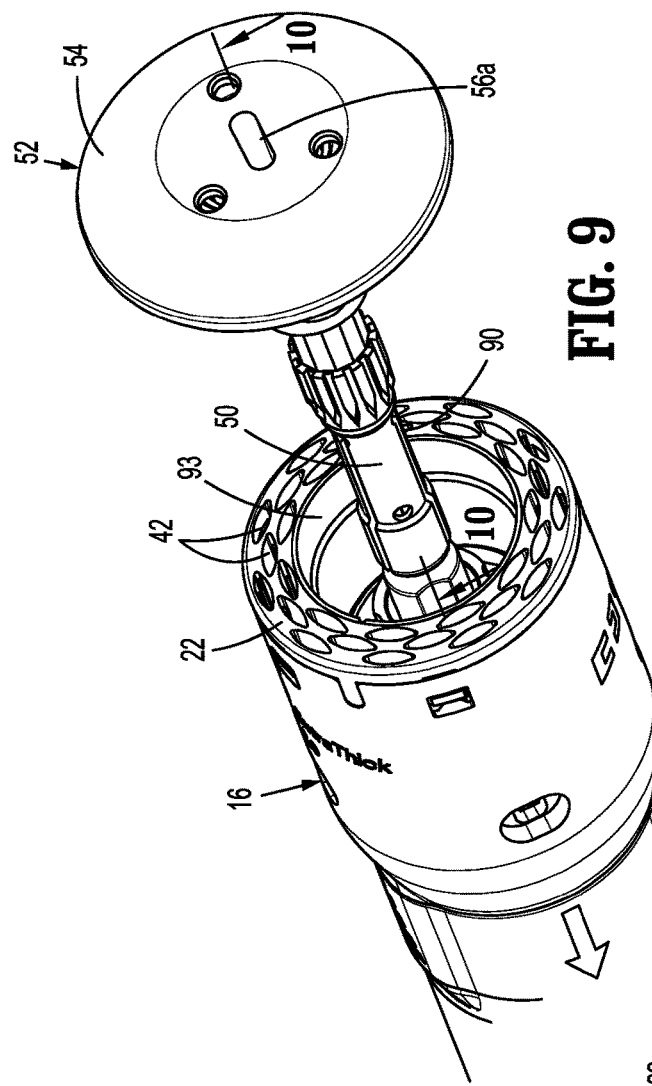
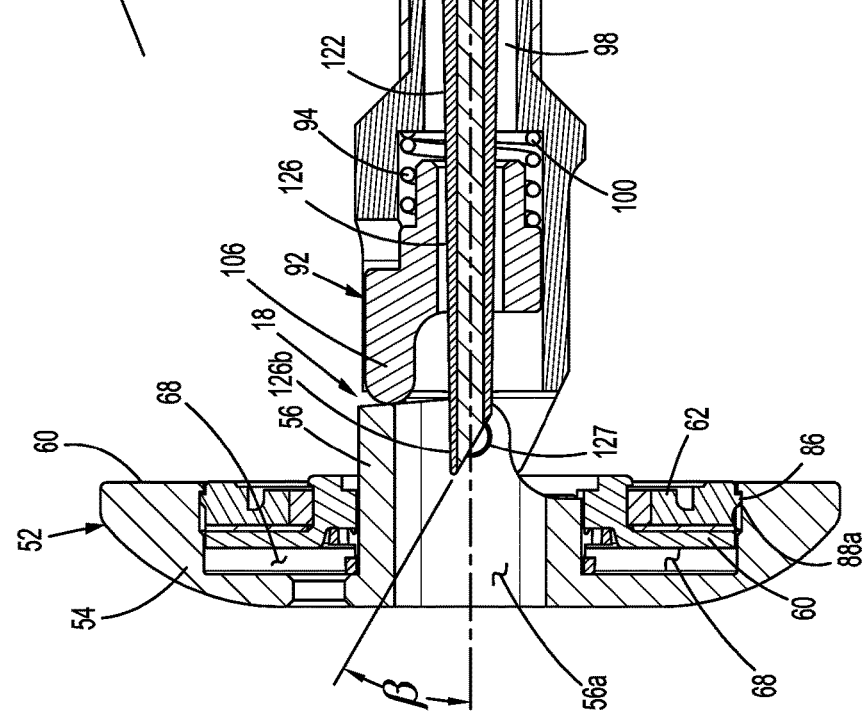
FIG. 9
FIG. 10

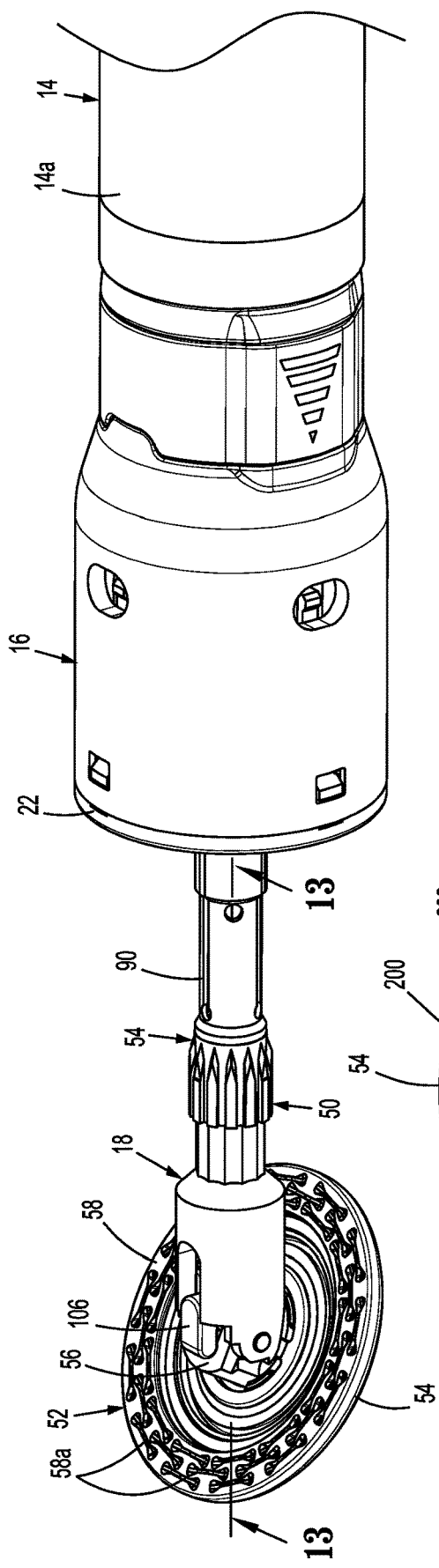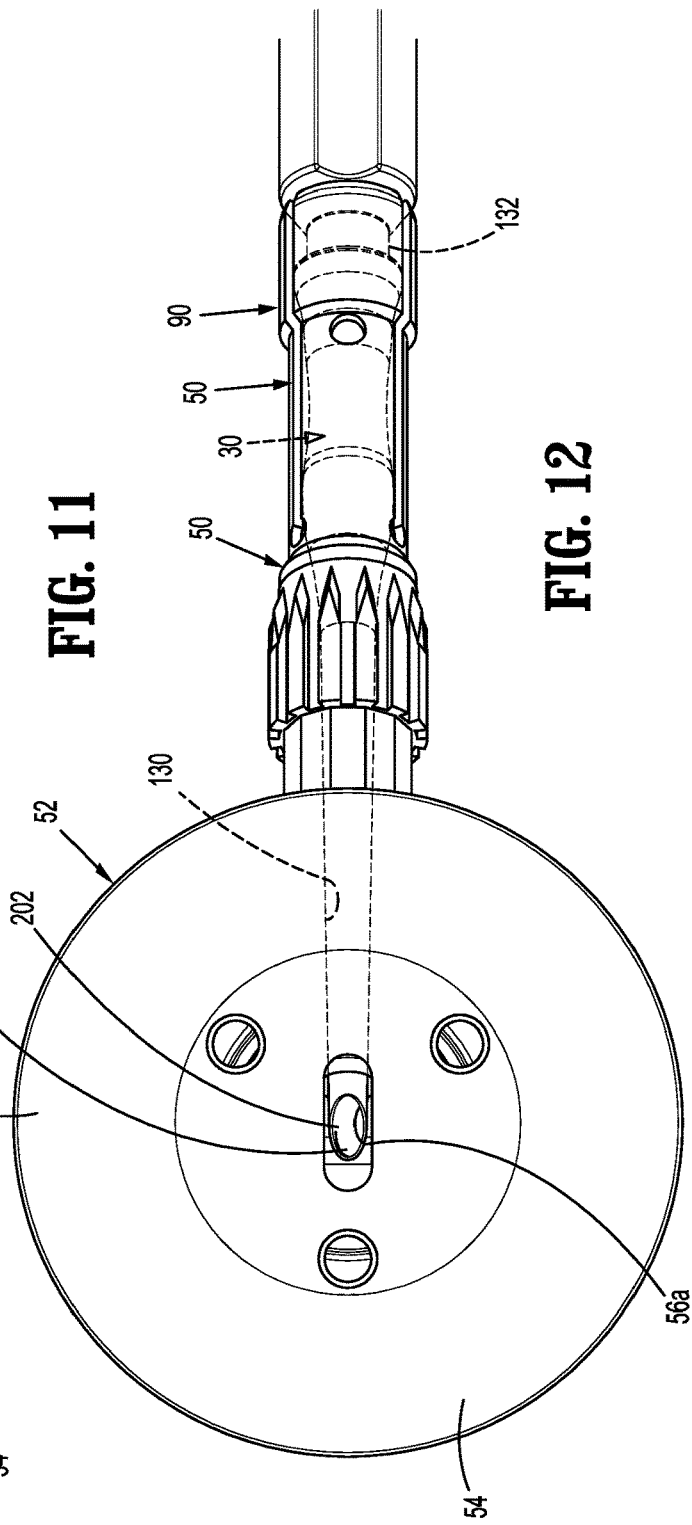
FIG. 11
FIG. 12

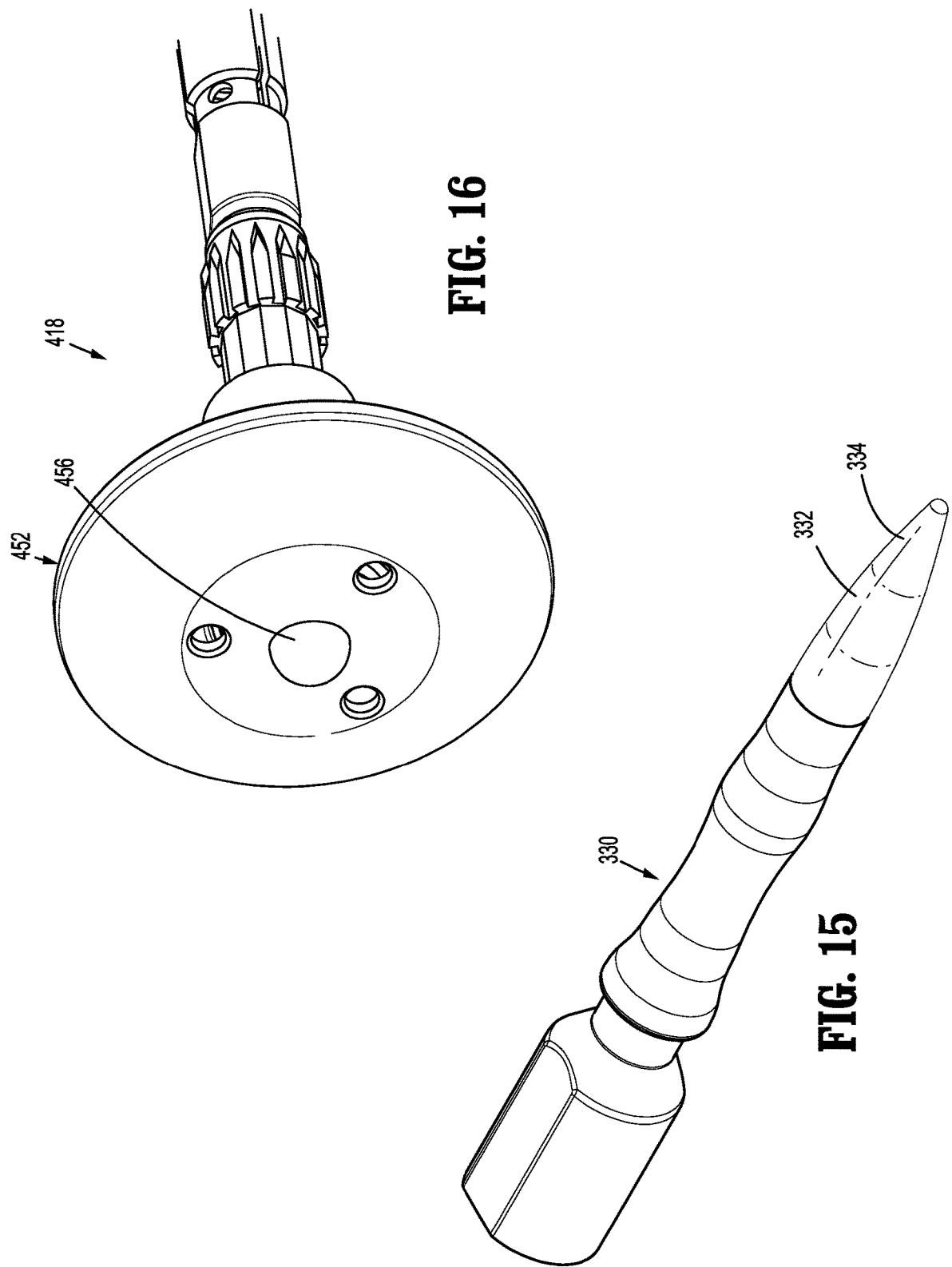

CIRCULAR STAPLING DEVICE WITH INTEGRATED VISUALIZATION DEVICE

CROSS-REFERENCE TO RELATED APPLICATION

This application claims the benefit of and priority to U.S. Provisional Patent Application No. 63/143,405, filed Jan. 29, 2021, the entire contents of which is incorporated by reference herein.

FIELD

The disclosure is directed to a stapling device, and more particularly, to a surgical stapling device with an integrated visualization device for intra-luminal visualization.

BACKGROUND

Circular stapling devices are commonly used to perform anastomoses during surgical procedures such as esophagogastrectomy, esophagoenterostomy, gastroenterostomy, and coloproctostomy. Anastomosis is the surgical connection of two body lumens, e.g., blood vessels, intestine, etc. Leaks in an anastomosis can lead to bleeding and result in infection which may result in life-threatening complications. As such, it is common practice for a clinician to examine the anastomosis after the anastomosis is formed to verify that there are no leaks or bleeding. Examination of the anastomosis typically requires an endoscopy procedure which is performed after the anastomosis procedure has been performed. This adds cost and time to the anastomosis procedure.

A continuing need exists in the surgical arts for a quicker, less expensive method for performing an anastomosis procedure.

SUMMARY

This disclosure is directed to a surgical stapling device that includes a visualization device that extends through a body of the stapling device to facilitate visualization of tissue that surrounds an end effector of the stapling device. This disclosure is also directed to an anvil assembly for a surgical stapling device that is adapted to facilitate passage of a visualization device to allow for visualization of tissue that surrounds the anvil assembly.

One aspect of the disclosure is directed to a surgical stapling device including an elongate body, an anvil retainer, an anvil assembly, and a visualization device. The elongate body has a proximal portion and a distal portion. The anvil retainer is positioned within the elongate body and movable between retracted and advanced positions. The anvil retainer has a proximal portion and a distal portion and defines a longitudinally extending through bore. The anvil assembly is coupled to the anvil retainer and includes an anvil head assembly and a center rod assembly that defines a longitudinal axis. The center rod assembly defines a through bore and has a proximal portion and a distal portion. The anvil head assembly is coupled to the distal portion of the center rod assembly and defines a through bore that is aligned with the through bore of the center rod assembly. The through bores of the center rod assembly and the anvil head assembly are aligned with the longitudinally extending through bore of the anvil retainer and the distal portion of the anvil retainer is positioned within the through bore of the anvil head assembly. The visualization device has a proximal portion and a distal portion. The distal portion of the visualization device extends through the through bores of the anvil retainer and the center rod assembly and is positioned within the through bore of the anvil head assembly. The visualization device is positioned to facilitate visualization of tissue surrounding the anvil head assembly of the anvil assembly.

In aspects of the disclosure, the visualization device includes an endoscope.

In some aspects of the disclosure, the visualization device is movable between retracted and advanced positions within the longitudinally extending through bore of the anvil retainer.

In certain aspects of the disclosure, in its advanced position, the visualization device is positioned distally of the anvil head assembly.

In aspects of the disclosure, the anvil head assembly is pivotably coupled to the center rod assembly between an operative position and a tilted position.

In some aspects of the disclosure, the anvil head assembly includes a housing, an anvil supported on the housing, and a post secured to the housing.

In certain aspects of the disclosure, the post is pivotably coupled to the center rod assembly.

In aspects of the disclosure, the through bore in the anvil head assembly extends through the post and the housing of the anvil head assembly and is elongated along an axis transverse to the longitudinal axis of the center rod assembly.

In some aspects of the disclosure, the surgical stapling device includes a handle assembly and the proximal portion of the elongate body is coupled to the handle assembly.

In certain aspects of the disclosure, the center rod assembly includes a center rod, a plunger, and a biasing member, and the center rod defines the through bore of the center rod assembly.

In aspects of the disclosure, the plunger includes a distally extending finger that is engaged with the anvil head assembly and the biasing member is engaged with the plunger to urge the plunger into the anvil head assembly to urge the anvil head assembly to its tilted position.

In some aspects of the disclosure, the plunger and the biasing member are received within the through bore of the center rod of the center rod assembly and the plunger defines a longitudinally extending through bore.

In certain aspects of the disclosure, the handle assembly includes a port for coupling the visualization device to a display device.

Another aspect of the disclosure is directed to an anvil assembly including an anvil head assembly and a center rod assembly that defines a longitudinal axis. The center rod assembly defines a through bore and has a proximal portion and a distal portion. The anvil head assembly is coupled to the distal portion of the center rod assembly and defines a through bore that is aligned with the through bore of the center rod assembly to define an unobstructed path through the anvil assembly.

Another aspect of the disclosure is directed to a surgical stapling device including an elongate body, an anvil retainer, and a visualization device. The elongate body has a proximal portion and a distal portion. The anvil retainer is positioned within the elongate body and is movable between retracted and advanced positions. The anvil retainer has a proximal portion and a distal portion and defines a longitudinally extending through bore. The visualization device has a proximal portion and a distal portion and extends through the through bore of the anvil retainer. The visualization device positioned to facilitate visualization of tissue surrounding the anvil retainer.

Other features of the disclosure will be appreciated from the following description.

BRIEF DESCRIPTION OF THE DRAWINGS

Various aspects of the disclosure are described herein below with reference to the drawings, wherein:

FIG. 6 is a side perspective view from the distal end of an anvil retainer of the circular stapling device shown in FIG. 1;

FIG. 7 is a side perspective view from the proximal end of the anvil retainer shown in FIG. 6;

FIG. 8 is a side view of the anvil retainer shown in FIG. 7;

FIG. 9 is a side perspective view of a distal portion of the circular stapling device shown in FIG. 1 with the anvil assembly attached to the anvil retainer and the anvil head assembly in an operative position;

FIG. 10 is a cross-sectional view taken along section line 10-10 of FIG. 9;

FIG. 11 is a side perspective view of the distal portion of the circular stapling device shown in FIG. 1 with the anvil assembly attached to the anvil retainer and the anvil head assembly in a tilted position;

FIG. 12 is a side perspective view of the anvil assembly and anvil retainer of the distal portion of the circular stapling device shown in FIG. 11;

FIG. 15 is an alternate version of the anvil retainer shown in FIG. 8; and

FIG. 16 is a side perspective view from the distal end of an alternate version of the anvil assembly of the stapling device shown in FIG. 1.

DETAILED DESCRIPTION

Figure 1:
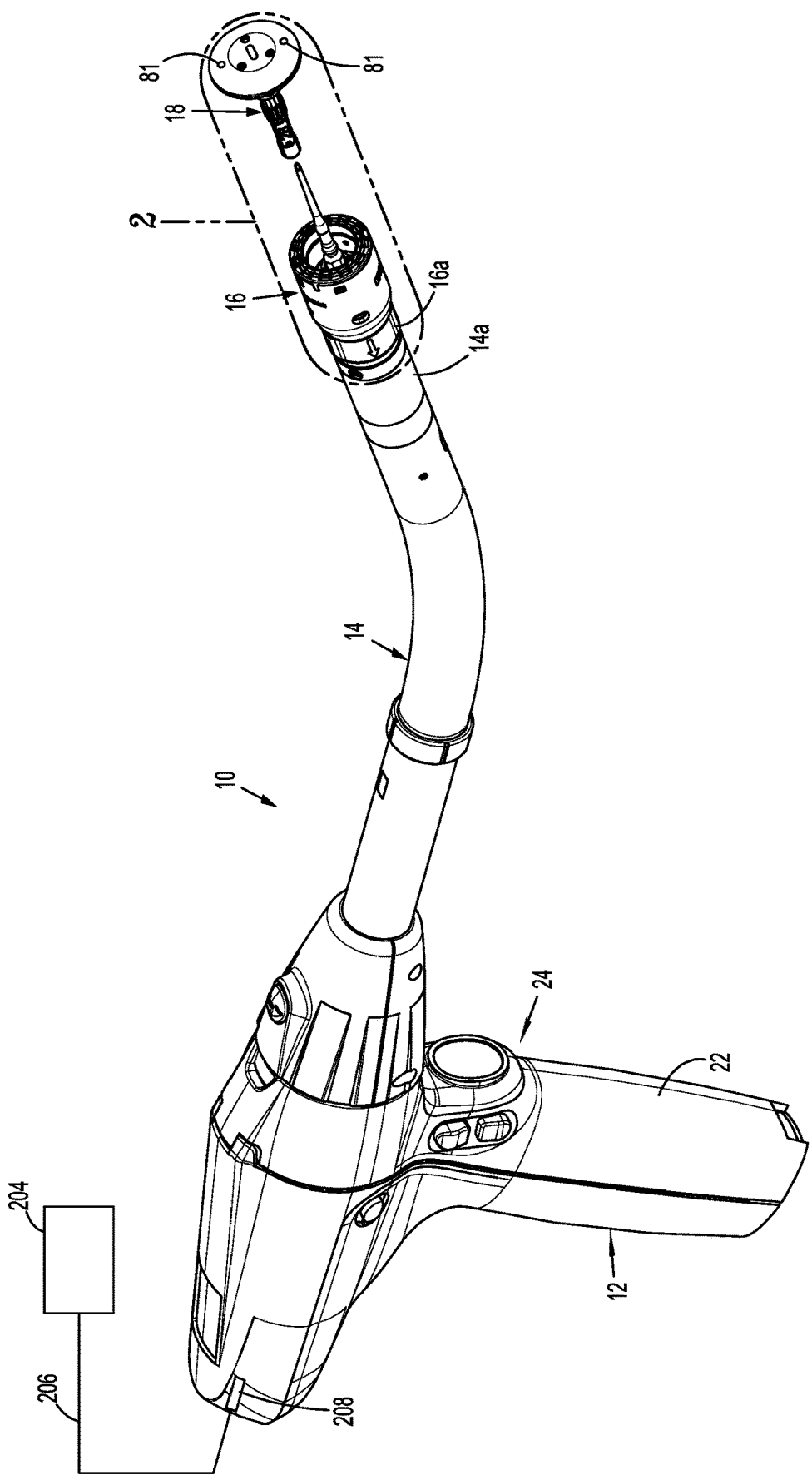
FIG. 1 is a side perspective view of a circular stapling device according to aspects of the disclosure with an anvil assembly separated from an anvil retainer of the circular stapling device.

The disclosed circular stapling device with integrated visualization device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 2:
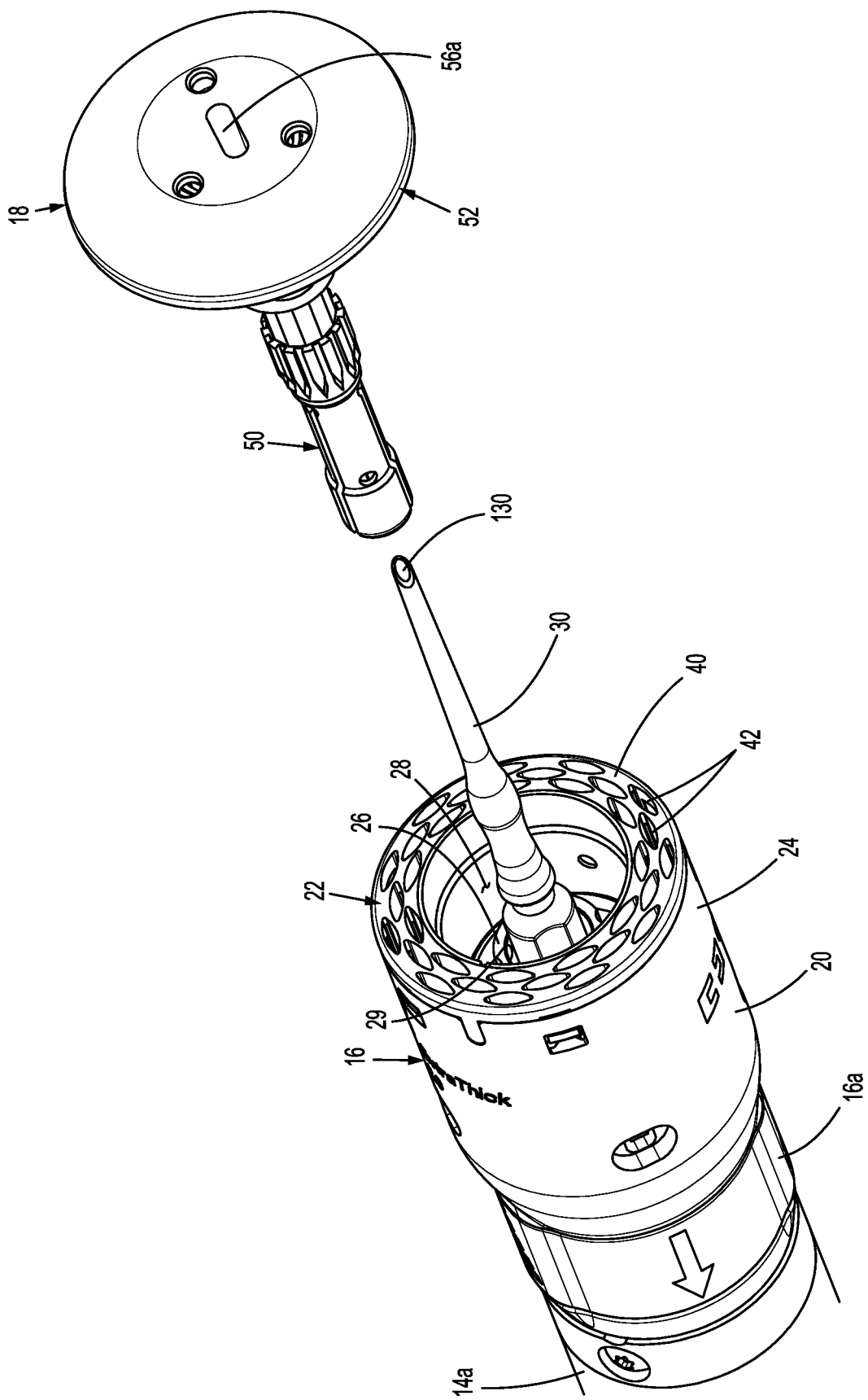
FIG. 2 is an enlarged view of the indicated area of detail shown in FIG. 1.

FIGS. 1 and 2 illustrate a circular stapling device according to aspects of the disclosure shown generally as stapling device 10. The stapling device 10 includes a handle assembly 12, an elongate body or adaptor assembly 14, a reload assembly 16, and an anvil assembly 18. The anvil assembly 18 is releasably supported on a distal end of the adaptor assembly 14 and is movable in relation to the reload assembly 16 between spaced and clamped positions as is known in the art. The reload assembly 16 includes a proximal portion 16a that is releasably coupled to a distal portion 14a of the elongate body 14. Alternately, the reload assembly 16 can be fixedly secured to the distal portion 14a of the elongate body 14. In certain aspects of the disclosure, the handle assembly 12 includes a stationary grip 22 that supports actuation buttons 24 for controlling operation of various functions of the stapling device 10 including approximation of the reload and anvil assemblies 16 and 18, respectively, firing of staples from the reload assembly 16, and cutting or coring of tissue.

The stapling device 10 is illustrated as an electrically powered stapling device and the handle assembly 12 is electrically powered and may support one or more batteries (not shown). The elongate body 14 is in the form of an adaptor assembly that translates power from the handle assembly 12 to the reload and anvil assemblies 16 and 18. Examples of electrically powered stapling devices can be found in U.S. Pat. Nos. 9,055,943, 9,023,014, and U.S. Publication Nos. 2018/0125495, and 2017/0340351. Alternately, it is envisioned that the stapling device 10 could also be a manually powered stapling device such as disclosed in U.S. Pat. No. 7,303,106 (the '106 patent) or a stapling device that is configured for use with a robotic system such as disclosed in U.S. Pat. No. 9,962,159 that does not include a handle assembly.

FIG. 2 illustrates a distal portion of the stapling device 10 (FIG. 1). The reload assembly 16 of the stapling device 10 includes a shell housing 20 and a staple cartridge 22 that is supported on the shell housing 20. The shell housing 20 includes an annular outer body portion 24 and an annular inner body portion 26 that defines a through bore 29. An anvil retainer or trocar 30 extends from the elongate body 14 through the through bore 29 in the shell housing 20 and extends from a distal end of the shell housing 20. The anvil retainer 30, which is described in further detail below, is configured to be releasably coupled to the anvil assembly 18 and is movable between advanced and retracted positions to move the anvil assembly 18 in relation to the staple cartridge 22 between the open and clamped positions.

The staple cartridge 22 includes an annular body 40, e.g., circular, that is supported on the shell housing 20. The annular body 40 of the staple cartridge 22 defines a plurality of staple pockets 42 that receive staples (not shown). In aspects of the disclosure, the staple pockets 42 are arranged in annular rows within the annular body 40 of the staple cartridge 22. Although three annular rows of staple pockets are illustrated, it is envisioned that the staple cartridge could have one or more rows of staple pockets 42.

Figure 3:
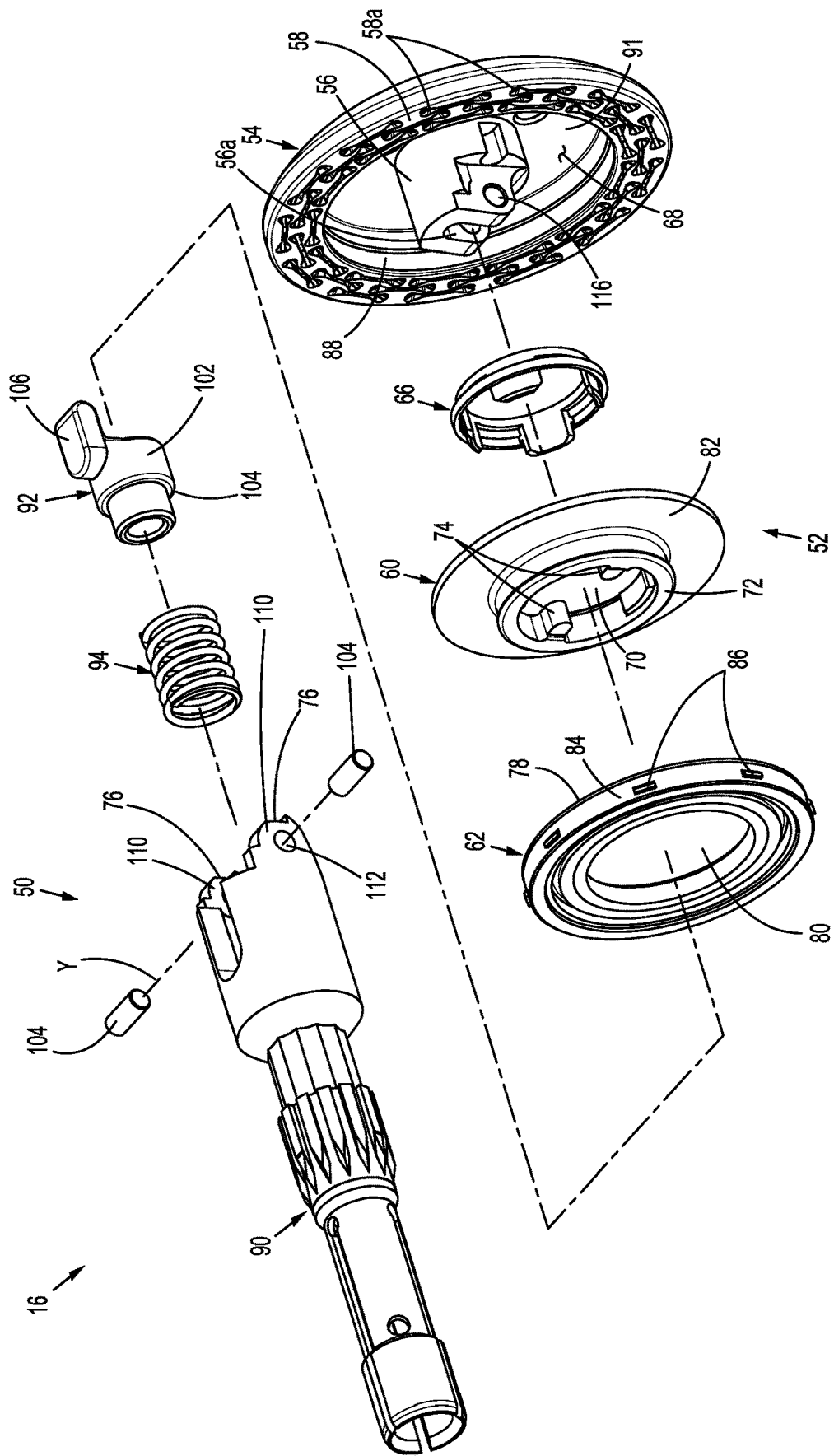
FIG. 3 is a side perspective, exploded view of the anvil assembly of the circular stapling device shown in FIG. 1.
Figure 4:
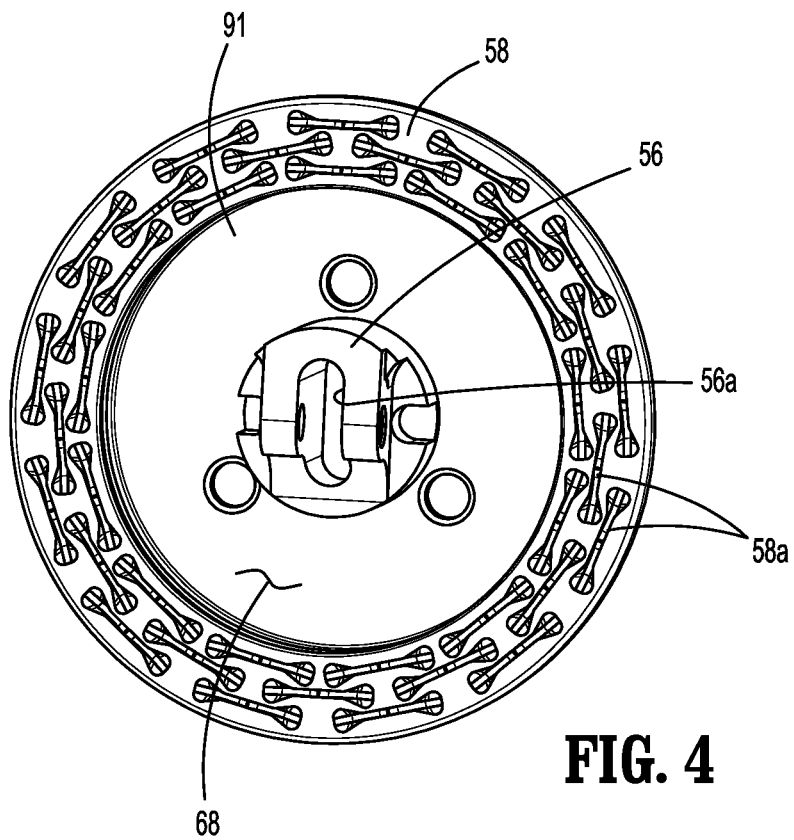
FIG. 4 is a view from the proximal end of an anvil head assembly of the anvil assembly shown in FIG. 3.

FIGS. 3 and 4 illustrate the anvil assembly 16 which includes a center rod assembly 50 and an anvil head assembly 52 that is pivotally supported on a distal portion of the center rod assembly 50. The anvil head assembly 52 includes a housing 54, a post 56, an anvil 58, a backup member 60, a cut ring 62, and a deformable support member 66. The housing 54 of the anvil head assembly 52 defines a cavity 68. The post 56 is supported on the housing 54 and is centrally located within the cavity 68. The post 56 and the housing 54 define a longitudinally extending through bore 56a (FIG. 4) that extends through the anvil head assembly 52. In aspects of the disclosure, the through bore 56a has an elongated configuration along an axis transverse to a longitudinal axis of the post 56, e.g., oval configuration. Alternately, the through bore 56a can have a variety of configurations including rectangular, circular, trapezoidal, etc. The anvil 58 is annular, e.g. circular, and is supported about the outer periphery of the housing 54. In aspects of the disclosure, the housing 54, the post 56, and the anvil 58 are monolithically formed. Alternately, any one or all the housing 54, post 56, and anvil 58 can be formed separately and secured together using any known fastening technique including welding, crimping or the like. The anvil 58 defines a plurality of staple deforming pockets 58a that receive and deform staples ejected from the reload assembly 14 when the stapling device 10 (FIG. 1) is fired.

The backup member 60 and the cut ring 62 are received within the cavity 68 of the housing 54. The backup member 60 defines a central opening 70 that receives the post 56 of the housing 54 of the anvil head assembly 52 to facilitate movement of the backup member 60 about the post 56 from a retracted position to an advanced position within the cavity 68 of the housing 54. The backup member 60 includes a raised annular flange 72 that is positioned about the opening 70. Although the raised flange 72 is illustrated as having a circular shape, other configurations are envisioned, e.g., square, rectangular, triangular, etc.

The backup member 60 includes a pair of inwardly extending fingers 74 that are movable into and out of engagement with distal flats 76 of the center rod assembly 50 of the anvil assembly 16. When the fingers 74 are engaged with the distal flats 76, the engagement prevents pivotal movement of the anvil head assembly 52 in relation to the center rod assembly 50. When the backup member 60 moves out of engagement with the distal flats 76, the anvil head assembly 52 can pivot in relation to the center rod assembly 50 between an operative position (FIG. 11) and a tilted position (FIG. 12). In aspects of the disclosure, the backup member 60 is formed from a hard material such as metal although other materials of construction are envisioned. In the tilted position, the profile of the anvil head assembly 52 is minimized to allow the anvil assembly 16 to be delivered to and removed from a body cavity through a body lumen, e.g., the esophagus, with minimal trauma to the body lumen. See U.S. Pat. No. 7,303,106 (hereinafter "'106 patent") for a detailed description of the operation and construction of a tiltable anvil assembly.

In aspects of the disclosure, the cut ring 62 includes a circular body 78 that defines a central opening 80 that receives the raised flange 72 of the backup member 60 and is aligned with the opening 70 in the backup member 60. The cut ring 62 is received about the flange 72 of the backup member 60 and is secured to a proximal surface 82 of the backup member 60. In certain aspects of the disclosure, the cut ring 62 is press-fit onto the raised flange 72 of the backup member 60 to secure the body 78 of the cut ring 62 onto the backup member 76.

The body 78 of the cut ring 62 includes an outer wall 84 that has a series of projections 86 and the housing 54 of the anvil head assembly 52 includes an inner wall 88 that defines an annular groove 88a (FIG. 10). In aspects of the disclosure, the projections 86 of the cut ring 62 are slidably received within the annular groove 88a in the housing 54 of the anvil head assembly 52 to guide movement of the cut-ring 62 and backup member 60 between their advanced and retracted positions within the cavity 68 of the housing 54 of the anvil assembly 16.

The deformable support member 66 is supported about the post 56 of the housing 54 of the anvil head assembly 52 between a proximal surface of the backup member 60 and an inner surface 91 of the housing 54. The deformable support member 66 retains the backup member 60 and the cut ring 62 in their retracted positions within the recess 68 of the housing 54 until a pre-determined force sufficient to deform the support member 66 is applied to the cut ring 62 during firing of the stapling device 10 (FIG. 1). During firing of the stapling device 10, a knife 93 (FIG. 9) of the reload assembly 16 (FIG. 1) is driven into the cut ring 62 to advance the cut ring 62 and back up member 60 into the cavity 68 of the housing 54 of the anvil head assembly 52 to deform the support member 66.

Figure 5:
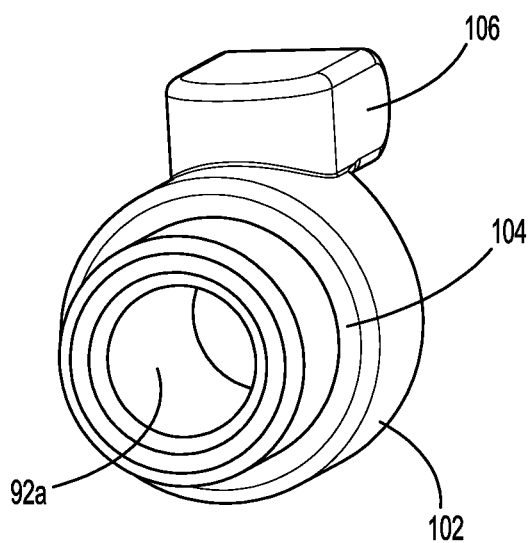
FIG. 5 is a perspective view from the proximal end of a plunger of a center rod assembly of the anvil assembly shown in FIG. 3.

The center rod assembly 50 includes a center rod 90, a plunger 92, and a plunger biasing member 94. The center rod 90 defines a stepped longitudinal bore 98 (FIG. 10). A proximal portion of the longitudinal bore 98 is defined by spaced resilient legs 96 that are deformable outwardly to releasably engage the anvil retainer 30 to secure the anvil assembly 18 to the anvil retainer 30. A distal portion of the longitudinal bore 98 receives the plunger 92 and the biasing member 94 (FIG. 10). The distal portion of the longitudinal bore 98 defines an annular shelf 100 (FIG. 10). The plunger 92 defines a longitudinally extending through bore 92a (FIG. 5) and includes a stepped body 102 that includes a proximally facing annular shoulder 104 and a distally extending finger 106. In aspects of the disclosure, the biasing member 94 includes a coil spring that is compressed between the annular shelf 100 of the center rod 90 and the annular shoulder 104 of the plunger 92 within the distal portion of the longitudinal bore 98 to urge the finger 106 of the plunger 92 distally into engagement with the post 56 of the anvil head assembly 52. Engagement of the finger 106 of the plunger 92 with the post 56 of the anvil head assembly 52 urges the anvil head assembly 52 towards its tilted position.

The center rod 90 of the anvil assembly 18 includes spaced arms 110 (FIG. 3) that define a clevis. Each of the spaced arms 110 includes one of the distally facing flats 76 and defines a transverse through bore 112. The transverse through bores 112 define an axis "Y" that intersects a central longitudinal axis "X" of center rod 90. Alternately, the axis "Y" defined by the through bores 112 can be laterally offset from the longitudinal axis "X" of center rod 90.

The post 56 of the housing 54 of the anvil head assembly 52 is positioned between the spaced arms 110 of the center rod 90 and defines a transverse through bore 116. A pivot member 104 extends through each of the through bores 112 and into the through bore 116 of the post 56 to pivotally secure the post 56 to the center rod 90 such that the anvil head assembly 52 is pivotally mounted to the center rod assembly 50 about the axis "Y" between the operative position (FIG. 10) and the tilted position (FIG. 11). In the operative position, the longitudinal axis "X" of the center rod 90 is axially aligned with a longitudinal axis of the post 56 of the anvil head assembly 52 and the anvil 58 faces the reload assembly 14. In the tilted position, the longitudinal axis "X" of the center rod 90 and the longitudinal axis of the post 56 define an acute angle. The distally facing flats 76 formed on the distal ends of the spaced arms 110 of the center rod 90 abut the inwardly extending fingers 74 of the backup member 60 when the backup member 60 is in its retracted position within the cavity 68 of the housing 54 of the anvil head assembly 52 to releasably retain the anvil head assembly 52 in the operative position (FIG. 10).

FIGS. 6-8 illustrate the anvil retainer 30 which includes a body 118 having a proximal portion 120 and a distal portion 122. The proximal portion 120 includes a coupling section 124 that is fixedly coupled to an approximation mechanism (not shown) of the stapling device 10 (FIG. 1). The '106 patent describes a coupling arrangement between an anvil retainer and an approximation mechanism of a stapling device suitable for use with stapling device 10. The distal portion 122 forms a trocar member 126 that has a diameter that decreases from its proximal end 126a towards its distal end 126b to facilitate passage of the trocar member 126 through tissue during a surgical procedure. In aspects of the disclosure, the distal end 126b of the trocar member 126 defines an opening 127 (FIG. 6) and includes an angled tip 128 that defines an angle Ω (FIG. 8) with a longitudinal axis "Z" of the anvil retainer 30. In some aspects of the disclosure, angle is from about 30 to about 60 degrees. In certain aspects of the disclosure, angle Ω is about 45 degrees. In some aspects of the disclosure, the opening 127 in the distal portion 122 of the trocar member 126 of the anvil retainer 30 can include a transparent cover 127a or the trocar member 126 can be formed of a transparent material to assist in visualization of an anastomotic site.

The body of the anvil retainer 30 defines a longitudinally extending through bore 130 (FIG. 10) and an annular engagement surface 132 (FIG. 7). The annular engagement surface 132 is engaged by engagement surfaces 96a (FIG. 10) of the resilient legs 96 of the center rod 90 of the anvil assembly 18 when the anvil assembly 18 is attached to the anvil retainer 30 to releasably secure the anvil assembly 18 to the anvil retainer 30. For a detailed description of the engagement between the anvil retainer 30 and the flexible legs 96 of the center rod 90, see the '106 patent. The longitudinally extending through bore 130 extends the length of the anvil retainer 30 and is aligned with the through bore 56a defined by the post 56 and the housing 54 of the anvil head assembly 52.

FIGS. 9 and 10 illustrate the distal portion of the stapling device 10 (FIG. 1) with the anvil assembly 18 attached to the anvil retainer 30 and the anvil assembly 18 in an unclamped position and the anvil head assembly 52 in the operative position. When the anvil assembly 18 is attached to the anvil retainer 30, the distal end 126b of the anvil retainer 30 is received within the elongated through bore 56a of the anvil head assembly 52. As illustrated, a visualization device 200 is inserted through the longitudinally extending through bore 130 in the body of the anvil retainer 30. The visualization device 200, which may be in the form of an endoscope, e.g., a camera, a gastroscope or colonoscope, has a proximal portion (not shown) and a distal portion 202. The proximal portion extends into the handle assembly 12 (FIG. 1) and is coupled to a display device 204 such as a monitor. The display device 204 can be coupled to the visualization device 200 by an appropriate connector 206. In that respect, the handle assembly 12 may include a port 208 for coupling the visualization device 200 to the connector 204. It is also envisioned that the display device 204 can be supported on or integrated with the handle assembly 12.

The distal portion 202 of the visualization device 200 is positioned adjacent the opening 127 in the distal end of the anvil retainer 30 such that the distal portion 202 (FIG. 12) of the visualization device 200 is positioned within the longitudinally extending elongated through bore 56a defined in the post 56 and the housing 54 of the anvil head assembly 52 of the anvil assembly 18. In aspects of the disclosure, the distal end of the visualization device 200 is directed at a viewing angle β with respect to the longitudinal axis "X" of the center rod 90 of the anvil assembly 18.

Figure 13:
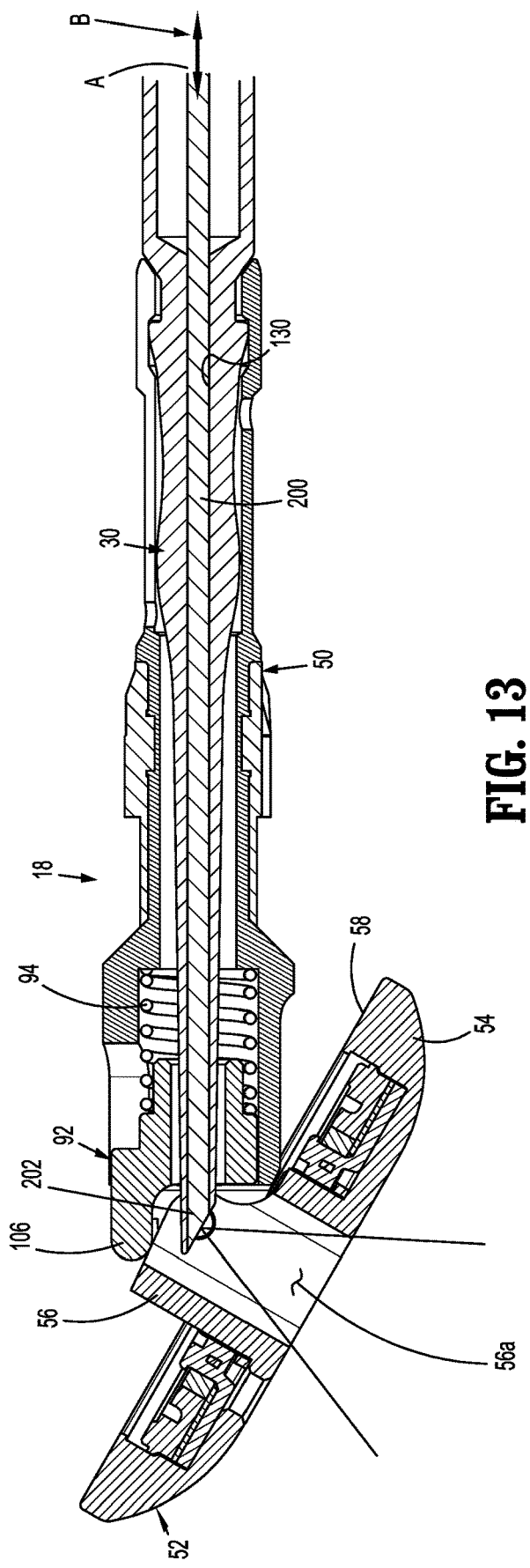
FIG. 13 is a cross-sectional view taken along section line 13-13 of FIG. 11.

FIGS. 11-13 illustrate the distal portion of the stapling device 10 (FIG. 1) with the anvil assembly 18 attached to the anvil retainer 30 and the anvil head assembly 52 of the anvil assembly 18 in a tilted position. As illustrated, when the anvil head assembly 52 tilts in relation to the center rod assembly 50, the distal end of the visualization device 200 is positioned to visualize tissue positioned about the anvil head assembly 52 through the elongated through bore 56a in the anvil head assembly 52. The viewing angle θ is selected to allow visualization of surrounding tissue when the anvil head assembly 52 is in a tilted position.

In aspects of the disclosure, the visualization device 200 is movable longitudinally between retracted and advanced positions within the longitudinally extending through bore 130 of the anvil retainer 30 in the directions indicated by arrows "A" and "B" in FIG. 13. In the retracted position, the distal end of the visualization device 200 is recessed within the through bore 130 of the anvil retainer 30 within the through bore 56a of the anvil head assembly 52. In the retracted position, the distal end of the visualization device 200 extends from the opening 127 in the distal end of the anvil retainer 30 and from the through bore 56a in the anvil head assembly 52 to a position distally of the anvil head assembly 52. In the advanced position, the visualization device 200 can visualize surrounding tissue when the anvil head assembly 52 of the anvil assembly 18 is in the operative position.

In an alternative aspect of the disclosure, the visualization device 200 can be fixedly retained within the through bore 130 of the anvil retainer 30 and need not be movable longitudinally.

FIG. 15 illustrates an alternate version of the anvil retainer shown generally as anvil retainer 330. The anvil retainer 330 is substantially the same as the anvil retainer 30 (FIG. 8) except that a distal end of the anvil retainer 330 does not include an angled tip. In contrast, the distal end of the anvil retainer 330 supports a transparent cover 332 that includes a tapered tip 334. The distal portion 202 of the visualization device 200 is positioned within the transparent cover 332 such that the visualization device 200 can visualize surrounding tissue through the transparent cover 332.

FIG. 16 illustrates an alternate version of the anvil assembly of the stapling device shown in FIG. 1 shown generally as anvil assembly 418. The anvil assembly 418 does not include a through bore, such as through bore 56a (FIG. 13). In contrast, the anvil assembly 418 includes an anvil head assembly 452 that has an outer surface 454 that supports a visualization device 456, e.g., a camera. In aspects of the disclosure, the visualization device 456 can have a dome-shaped lens to facilitate better visualization of the anastomotic site. In some aspects of the disclosure, the visualization device 456 can be battery powered and transmit images wirelessly to a monitor to allow a clinician to visualize the anastomotic site. In certain aspects of the disclosure, the power source for the camera, e.g., battery, can be disposed remotely from the anvil assembly 418. In such instances, the stapling device 10 (FIG. 1) can include an electrical loop (not shown) which is closed when the anvil assembly 418 is properly attached to the anvil retainer 30 (FIG. 2) to provide power to the visualization device 456.

In aspects of the disclosure, an irrigation channel is provided within the stapling device 10 to clean the visualization device prior to visualization of the anastomotic site. The irrigation channel can also be used as an insufflation channel for insufflating a body cavity. In addition, a light source 81 (FIG. 1) can be supported on the stapling device 10 to illuminate the anastomotic site prior to visualization.

The disclosed stapling device 10 allows a clinician to inspect tissue surrounding the anvil head assembly 52 of the anvil assembly 18 without having to insert a separate endoscope into a body lumen after a surgical procedure, e.g., an anastomosis procedure, has been performed. The disclosed stapling device 10 also allows a clinician to inspect tissue surrounding the anvil head assembly 52 of the anvil assembly 18 prior to performing a surgical procedure to ensure that suitable tissue is being treated. It is also noted that the visualization device can also be used to assist the clinician when attaching the anvil assembly 18 to the anvil retainer 30.

Figure 14:
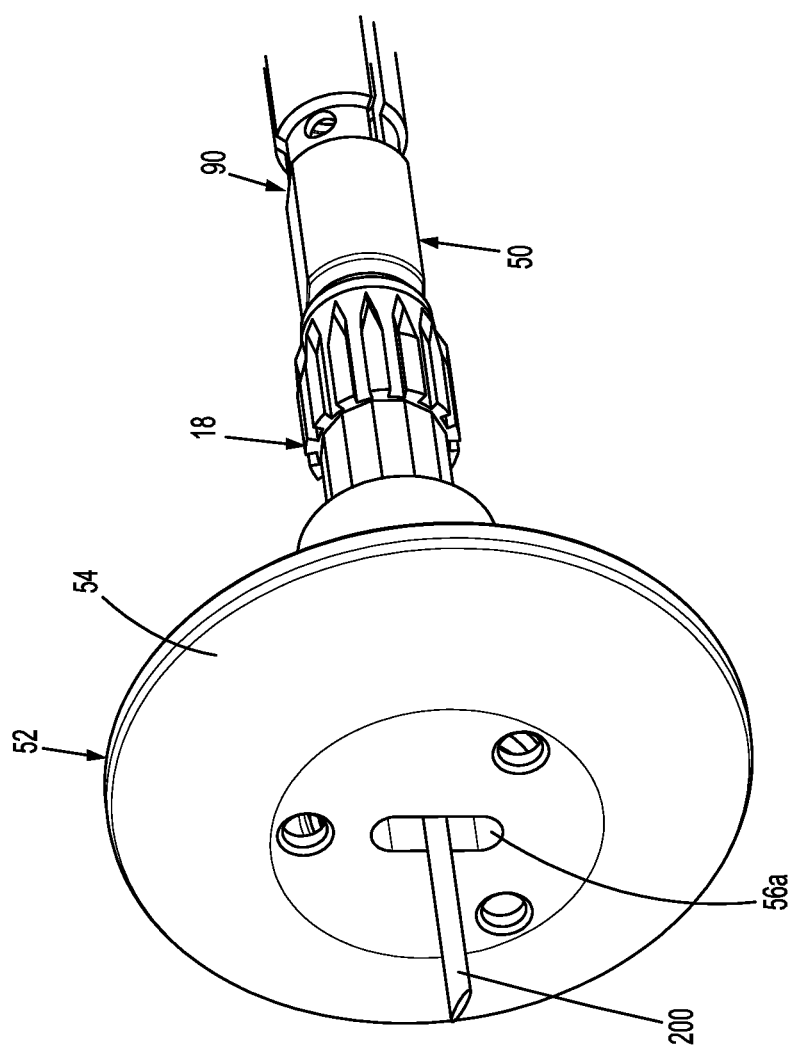
FIG. 14 is a side perspective view of a distal portion of the anvil assembly and visualization device of the anvil retainer shown in FIG. 13 with the anvil head assembly of the anvil assembly in the operative position and the visualization device in an extended position extending through the anvil head assembly of the anvil assembly.

It is noted that although the stapling device 10 is illustrated and described as including an anvil assembly 18 with a tiltable anvil head assembly 52, it is envisioned that the anvil head assembly 52 can be fixedly secured to the center rod assembly 50. In such a device, the visualization device 200 is movable to an extended position as described with reference to FIG. 14.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
   an elongate body having a proximal portion and a distal portion;
   an anvil retainer positioned within the elongate body and movable between retracted and advanced positions, the anvil retainer having a proximal portion and a distal portion and having a longitudinally extending through bore;
   an anvil assembly coupled to the anvil retainer, the anvil assembly including an anvil head assembly and a center rod assembly that has a longitudinal axis, the center rod assembly having a through bore and having a proximal portion and a distal portion, the anvil head assembly coupled to the distal portion of the center rod assembly and having a through bore that is aligned with the through bore of the center rod assembly, the through bores of the center rod assembly and the anvil head assembly being aligned with the longitudinally extending through bore of the anvil retainer and the distal portion of the anvil retainer positioned within the through bore of the anvil head assembly; and
   a visualization device having a proximal portion and a distal portion, the visualization device extending through the through bores of the anvil retainer and the center rod assembly and positioned within the through bore of the anvil head assembly, the visualization device positioned to facilitate visualization of tissue surrounding the anvil head assembly of the anvil assembly.

2. The surgical stapling device of claim 1, wherein visualization device includes an endoscope.

3. The surgical stapling device of claim 1, wherein the visualization device is movable between retracted and advanced positions within the longitudinally extending through bore of the anvil retainer.

4. The surgical stapling device of claim 3, wherein in its advanced position, the visualization device is positioned distally of the anvil head assembly.

5. The surgical stapling device of claim 1, wherein the anvil head assembly is pivotably coupled to the center rod assembly between an operative position and a tilted position.

6. The surgical stapling device of claim 5, wherein the anvil head assembly includes a housing, an anvil supported on the housing, and a post secured to the housing, the post being pivotably coupled to the center rod assembly.

7. The surgical stapling device of claim 6, wherein the through bore in the anvil head assembly extends through the post and the housing of the anvil head assembly and is elongated along an axis transverse to the longitudinal axis of the center rod assembly.

8. The surgical stapling device of claim 5, wherein the center rod assembly includes a center rod, a plunger, and a biasing member, the center rod having the through bore of the center rod assembly.

9. The surgical stapling device of claim 8, wherein the plunger includes a distally extending finger that is engaged with the anvil head assembly and the biasing member is engaged with the plunger such that the biasing member is configured to urge the plunger into the anvil head assembly to urge the anvil head assembly to its tilted position.

10. The surgical stapling device of claim 9, wherein the plunger and the biasing member are received within the through bore of the center rod of the center rod assembly and the plunger has a longitudinally extending through bore.

11. The surgical stapling device of claim 1, further including a handle assembly, the proximal portion of the elongate body coupled to the handle assembly.

12. The surgical stapling device of claim 11, wherein the handle assembly includes a port for coupling the visualization device to a display device.

13. An anvil assembly comprising:
   an anvil head assembly and a center rod assembly, the anvil head assembly pivotably coupled to the center rod assembly between an operative position and a tilted position, the center rod assembly including a longitudinal axis and a through bore and having a proximal portion and a distal portion, the anvil head assembly coupled to the distal portion of the center rod assembly and having a through bore that is aligned with the through bore of the center rod assembly in the operative position to form an unobstructed path through the anvil assembly.

14. The anvil assembly of claim 13, wherein the through bore of the center rod assembly and the anvil head assembly are positioned along the longitudinal axis of the center rod assembly in the operative position.

15. The anvil assembly of claim 14, wherein the anvil head assembly includes a housing, an anvil supported on the housing, and a post secured to the housing, the post being pivotably coupled to the center rod assembly.

16. The anvil assembly of claim 15, wherein the through bore in the anvil head assembly extends through the post and the housing of the anvil head assembly and is elongated along an axis transverse to the longitudinal axis of the center rod assembly.

17. The anvil assembly of claim 16, wherein the center rod assembly includes a center rod, a plunger, and a biasing member, the center rod including the through bore of the center rod assembly.

18. The anvil assembly of claim 17, wherein the plunger includes a distally extending finger that is engaged with the anvil head assembly and the biasing member is engaged with the plunger such that the biasing member is configured to urge the plunger into the anvil head assembly to urge the anvil head assembly to its tilted position.

* * * * *